(12) United States Patent
Zamarripa et al.

(10) Patent No.: US 9,445,758 B2
(45) Date of Patent: Sep. 20, 2016

(54) CHEMOCHROMIC MEDICAL ARTICLES

(71) Applicant: Boston Scientific Scimed Inc., Maple Grove, MN (US)

(72) Inventors: Nathan Zamarripa, Sudbury, MA (US); Jeff Gray, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/190,910

(22) Filed: Feb. 26, 2014

(65) Prior Publication Data

US 2014/0275908 A1  Sep. 18, 2014

Related U.S. Application Data

(60) Provisional application No. 61/780,117, filed on Mar. 13, 2013.

(51) Int. Cl.
| | |
|---|---|
| *A61B 5/1473* | (2006.01) |
| *A61B 10/00* | (2006.01) |
| *A61B 5/145* | (2006.01) |
| *A61B 5/15* | (2006.01) |
| *A61B 5/157* | (2006.01) |
| *A61B 5/20* | (2006.01) |
| *A61B 5/00* | (2006.01) |
| *A61M 25/00* | (2006.01) |
| *G01N 33/52* | (2006.01) |
| *G01N 21/78* | (2006.01) |
| *A61M 25/04* | (2006.01) |

(52) U.S. Cl.
CPC ......... *A61B 5/1473* (2013.01); *A61B 5/14507* (2013.01); *A61B 5/14532* (2013.01); *A61B 5/14546* (2013.01); *A61B 5/157* (2013.01); *A61B 5/150992* (2013.01); *A61B 5/207* (2013.01); *A61B 5/6852* (2013.01); *A61B 10/007* (2013.01); *A61M 25/00* (2013.01); *A61M 25/0017* (2013.01); *G01N 21/78* (2013.01); *G01N 33/52* (2013.01); *A61M 25/04* (2013.01)

(58) Field of Classification Search
CPC ............ A61B 5/1473; A61B 5/14546; A61B 5/150992; A61B 5/207; A61B 5/157; A61B 5/14532; A61B 5/14507; A61B 10/007; A61B 5/6852; A61M 25/0017; A61M 25/00; A61M 25/04; G01N 21/78; G01N 33/52
See application file for complete search history.

(56) References Cited

U.S. PATENT DOCUMENTS

| | | | | |
|---|---|---|---|---|
| 3,732,079 | A | * | 5/1973 | Davis ............................ 422/408 |
| 5,417,657 | A | * | 5/1995 | Hauer ...................... 604/103.02 |
| 5,645,824 | A | * | 7/1997 | Lim et al. .................... 424/70.1 |
| 5,938,595 | A | | 8/1999 | Glass et al. |
| 6,450,971 | B1 | | 9/2002 | Andrus et al. |
| 2002/0006355 | A1 | * | 1/2002 | Whitson ......................... 422/56 |
| 2002/0077680 | A1 | | 6/2002 | Noda |
| 2003/0216732 | A1 | * | 11/2003 | Truckai .................. A61B 18/14 606/49 |

(Continued)

OTHER PUBLICATIONS

O.B. Ayyub et al., "Color changing block copolymer films for chemical sensing of simple sugars," Biosensors and Bioelectronics 28 (2011), pp. 349-354.

(Continued)

*Primary Examiner* — Lore Jarrett

(57) ABSTRACT

The present invention is directed to medical articles which exhibit a color change upon exposure to an analyte of interest and to methods of detecting analytes in bodily fluid using the same.

20 Claims, 1 Drawing Sheet

(56) References Cited

U.S. PATENT DOCUMENTS

| | | | |
|---|---|---|---|
| 2005/0222591 A1 | 10/2005 | Gingras et al. | |
| 2010/0317092 A1* | 12/2010 | Suzuki | A61B 5/1411 435/287.1 |
| 2011/0031406 A1* | 2/2011 | Wirth | G01T 1/2018 250/363.02 |
| 2011/0040157 A1* | 2/2011 | Addington | A61B 5/04882 600/301 |
| 2012/0041479 A1 | 2/2012 | Basore et al. | |
| 2012/0059255 A1 | 3/2012 | Paul et al. | |
| 2012/0101515 A1 | 4/2012 | Barbod | |
| 2014/0069202 A1* | 3/2014 | Fisk | A61M 5/3129 73/762 |

OTHER PUBLICATIONS

Anne Trafton, "MIT gel changes color on demand," MIT 1 page. Downloaded from www.analytica-world.com on Dec. 17, 2012.

Andrey S. Klymchenko et al., "Electrochromic Modulations of Excited-State Intramolecular Proton Transfer: The New Principle in Design of Fluorescence Sensors," J. Am. Chem. Soc., vol. 124, No. 41, 2002, pp. 12372-12379.

Xiaobai Wang et al., "Synthesis, Electronic, and Emission Spectroscopy, and Electrochromic Characterization of Azulene-Fluorene Conjugated Oligomers and Polymers", Macromolecules, 2009, 42 (15), pp. 5534-5544 (Abstract).

"Photonic gels are colorful sensors," PHYSorg.com. Oct. 10, 2012, 3 pages.

"Materials: Switched-on color-changing polymers," published online Mar. 31, 2010, www.research.a-star.edu.sg/research/6127, 3 pages.

Y. Kang et al., "Broad-wavelength-range chemically tunable block-copolymer photonic gels," Nature Materials 6, 957-960 (2007) (Abstract).

Anne Trafton, "MIT gel changes color on demand"MIT Tech Talk, vol. 52, No. 6, Oct. 24, 2007, p. 4.

CN102564963 (Abstract), Ding et al., "Polyaniline nano fiber film vitamin C color sensor and detection method therof", Jul. 11, 2012, 1 page.

Ho Sun Lim, "Dynamic Swelling of Tunable Full-Color Block Copolymer Photonic Gels via Counterion Exchange," ACS Nano, 2012, 6 (10), 8933-8939 (Abstract).

Lizanel Feliciano, "Color Changing Plastics for Food Packaging," Ohio State University, Columbus, Ohio, 2009, pp. 1-13.

* cited by examiner

CHEMOCHROMIC MEDICAL ARTICLES

STATEMENT OF RELATED APPLICATION

This application claims the benefit of U.S. Ser. No. 61/780,117, filed Mar. 13, 2013 and entitled: "CHEMOCHROMIC MEDICAL ARTICLES," which is hereby incorporated by reference in its entirety.

FIELD OF THE INVENTION

The present invention relates to medical articles which exhibit a color change with exposure to an analyte of interest.

BACKGROUND

Bodily fluids are commonly analyzed for a wide range of substances (referred to herein as "analytes"), both endogenous and exogenous, for various purposes including, for example, the diagnosis and treatment of various diseases and conditions, the detection of drug use, and so forth.

In some analyses, it is desired to determine the precise amount (e.g., concentration) of an analyte of interest. In others, it is desired merely to determine whether or not an analyte of interest is present in any detectable amount or is present above a certain threshold amount. For example, bodily fluid analysis is often done in a hospital or clinical setting when there is a risk that the levels of certain analytes may move above a certain level or outside a desired range and adversely affect the health of a patient.

Many currently known systems for analyte monitoring in a hospital or clinical setting, however, suffer from delay in obtaining results, which could potentially jeopardize a patient's health.

SUMMARY OF THE INVENTION

The above and other drawbacks of the current state of the art are addressed by the present invention, which is directed to medical articles which exhibit a color change in conjunction with exposure to an analyte of interest.

In some aspects, the invention pertains to medical articles that are configured for exposure to a bodily fluid, wherein the medical article comprises a chemochromic material that exhibits a color change upon exposure to an analyte present in the bodily fluid.

In other aspects, the invention pertains to a method of detecting an analyte comprising (a) contacting a medical article that comprises a chemochromic material that exhibits a color change upon exposure to the analyte with a bodily fluid being tested for the presence of the analyte and (b) observing a color change, if any, in the chemochromic material.

An advantage of the present invention is that medical articles may be provided which offer prompt feedback regarding the presence an analyte of interest based on color changing technology.

Another advantage of the present invention is that medical articles may be provided which employ color changing polymer technology to promptly indicate specific diseases or conditions.

These and other aspects, embodiments and advantages of the present invention will become immediately apparent to those of ordinary skill in the art upon review of the detailed description and claims to follow.

DETAILED DESCRIPTION OF THE INVENTION

Figure 1A:
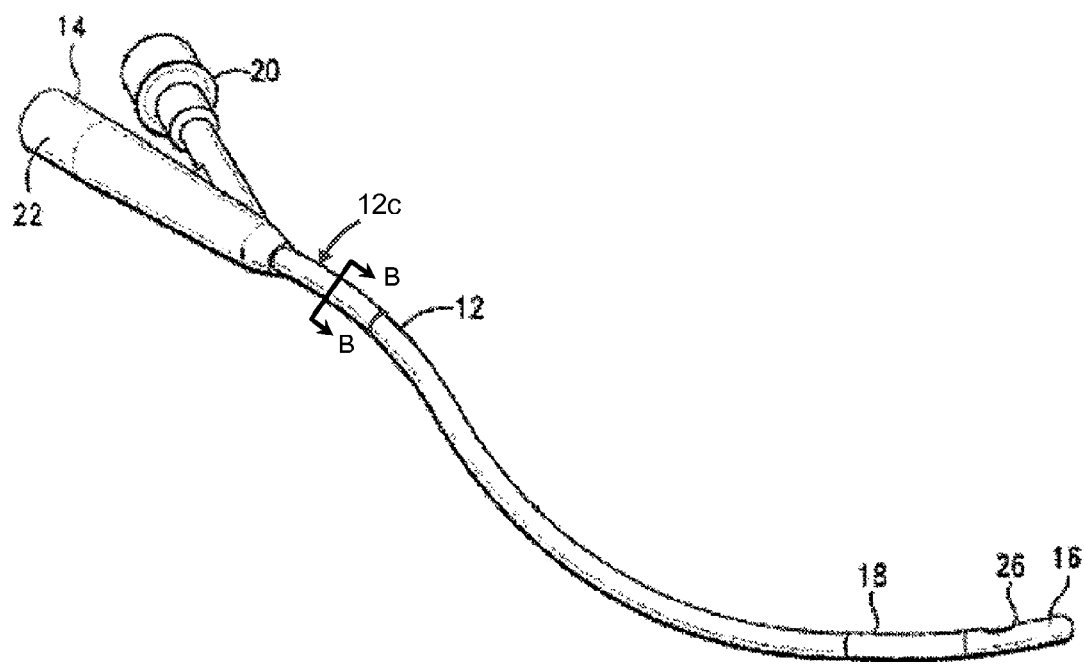
FIG. 1A is a schematic perspective view of a Foley catheter, according to an embodiment of the present invention.

A more complete understanding of the present invention is available upon reference to the following detailed description of various aspects and embodiments of the invention. The detailed description of the invention which follows is intended to illustrate but not limit the invention.

As previously noted, the present invention is directed to medical articles which exhibit a color change upon exposure to an analyte of interest. This behavior is achieved by providing the medical articles of the present disclosure with a chemochromic material. As used herein, a "chemochromic material" is a material that becomes colored, or changes color, upon exposure to a chemical species (e.g., an analyte) to which the chemochromic material is sensitive. Typically, an analyte of interest will be above a certain threshold concentration before a detectable color change occurs.

In certain embodiments, chemochromic materials for use in the present disclosure are formed from polymers, including block copolymers.

As used herein, "polymers" are molecules containing multiple copies of one or more constitutional units, commonly referred to as monomers. Polymers may take on a number of configurations, which may be selected, for example, from linear, cyclic, and branched configurations. Branched configurations include star-shaped configurations (e.g., configurations in which three or more chains emanate from a single branch point) and comb configurations (e.g., configurations having a main chain and a plurality of side chains), among others. As used herein, "homopolymers" are polymers that contain multiple copies of a single constitutional unit. As used herein, "copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in chemical composition, for instance, because a constitutional unit (i.e., monomer) is found in one polymer block that is not found in another polymer block. As used herein, a "polymer block" is a grouping of constitutional units (e.g., 5 to 10 to 25 to 50 to 100 to 250 to 500 to 1000 or more units) that forms part of a block polymer. Polymer blocks can be branched or unbranched. Polymer blocks can contain a single type of constitutional unit (also referred to herein as "homopolymer blocks") or two or more different types of constitutional units (also referred to herein as "copolymer blocks") which may be provided, for example, in a periodic (e.g., alternating), random, statistical or gradient distribution. The differing polymer blocks of a given block copolymer are typically immiscible with one another and separate into distinct phases (or "phase domains") when in solid form. The shape, size, and spacing of the elements associated with each phase domain may be controlled by a number of factors including the processing techniques that are used to form the phase domains, the overall size (molecular weight) of the polymer blocks, and the size of the differing polymer blocks relative to one another (which affects the relative volume of each phase domain), among other factors.

Medical articles in accordance with the present disclosure may be used to detect an analyte of interest for a variety of purposes including, for example, the diagnosis of various diseases and conditions, the treatment of various diseases and conditions, and drug detection, among others.

Analytes of interest thus include a wide range of endogenous and exogenous substances including inorganic substances, organic substances (e.g., including small molecule and polymeric organic compounds), nonionic substances, ionic substances (including anionic, cationic and zwitterionic substances), and so forth. Potentially detectable analytes of interest include those that are present in bodily fluids.

Medical articles in accordance with the present disclosure include those that are configured to come into contact with bodily fluids such as blood, urine, and gastric juices, among others. Specific examples of medical articles in accordance with the present disclosure include the following, among many others: urinary catheters, urine storage bags, venous catheters, arterial catheters, peripherally inserted central catheters (PICS), dialysis catheters, epidural catheters, drainage catheters, catheter tubing, catheter collection containers including collection bags, blood pumps, hemofliltration devices, stopcocks, fluid management manifolds, drainage tubing, drainage bags, bed pans, syringes, glucose meters, pericardial drainage/aspiration devices, enteral feeding devices, tracheal devices, ventricular assist devices, blood storage bags, blood drawing systems, Swan-Ganz catheters, embryo transfer catheters, umbilical line catheters, Tuohy-Borst adapters, Quinton catheters, intrauterine catheters, extracorporeal kidney assist devices, lung assist devices, grafts, bandages, wound dressings, dental implants, orthopedic implants, containment vessels which are used to transport or store body fluids, and laboratory articles such as assay trays, test tubes, centrifuge tubes, culture dishes and flasks, among many other articles.

As one specific example, a syringe typically used to draw blood may be made chemochromic and thus provide an indication regarding the presence of an analyte (e.g., above a minimum detection level for the analyte), simply by observing a color change as the syringe is filled with blood. Another specific example of a medical article is an assay tray in which small wells are arranged. These wells are typically filled with fluid to be tested offsite by sophisticated laboratory equipment such as mass spectrometers. Making the assay tray chemochromic may allow a positive/negative or true/false reading to be made by simply watching for a change in the color of the tray material as the fluid well is filled, thus providing an immediate, visibly discernible indication. As another specific example of a medical article, an external portion of a catheter (i.e., a portion of the catheter that is not inserted into the body) may be made chemochromic, allowing a healthcare professional to view a color change upon detection of an analyte.

Medical articles in accordance with the present disclosure include medical articles that can be checked by a health care professional periodically (e.g., once a day, twice a day, etc.) and medical articles that provide real-time results that can alert a health care professional to a developing problem, among other possibilities.

The chemochromic materials may be incorporated into the medical articles of the present disclosure in many different ways. For example, an entire medical article may be made chemochromic or only a portion of a medical article (including a component of a medical article) may be made chemochromic. The medical article or portion thereof may be formed entirely of a chemochromic material or may comprise a layer of chemochromic material disposed over an underlying material, among other possibilities.

Chemochromic materials for use in the present disclosure include those that have periodic (e.g., multi-layer) nano-structures that comprise first and second components of differing refractive index which interact with light, and whose interactions with light are modified upon contact with an analyte of interest. In various embodiments, these materials comprise polymers and have a multi-layer (also referred to as "lamellar") morphology. For example, as noted above, block copolymers are known to phase separate into a number of different morphologies depending on various factors including the relative sizes of each polymer block. For example, block copolymers comprising two blocks of approximately equal size are known to exhibit lamellar morphology. If there is sufficient contrast in refractive index between the two blocks in the lamellar structure then certain wavelengths of light can be reflected by the material, depending on the spacing between the layers.

Chemochromic materials can undergo a color change based on a number of different chemical interactions with an analyte of interest, including covalent binding and non-covalent binding. For instance, an analyte may bind to a chemochromic material via one or more of a variety of non-covalent binding mechanisms including, for example, those based van der Waals forces, hydrophobic interactions and/or electrostatic interactions (e.g., charge-charge interactions, charge-dipole interactions, and dipole-dipole interactions, including hydrogen bonding), among others. Some specific examples of non-covalent interactions include $\pi$-$\pi$ stacking, binding based on the formation of multiple hydrogen bonds (e.g., polynucleotide hybridization, etc.), binding based on the formation of complexes and/or coordinative bonds (e.g., metal ion chelation, etc.), binding based on antibody-antigen interactions, also sometimes referred to as antibody-hapten interactions, protein-small molecule interactions (e.g., avidin/streptavidin—biotin binding), protein-protein interactions, plasma-protein interactions, and so forth. Chemochromic materials for use in the present disclosure can be developed based on one or more of these interactions.

As a specific example of a chemochromic material, self-assembling, block copolymer thin films made of alternating layers of two polymer blocks, specifically, a polystyrene block and a poly-2-vinyl-pyridine block, have been developed. The thickness of the layers and their refractive indices determine what color light is reflected by the film. The thickness of the poly-2-vinyl-pyridine layer is altered with changes in pH and salt concentration, which results in an immediate observable change in color. See Y. Kang et al., *Nature Materials* 6, 957-960 (2007) and MIT Tech Talk, Volume 52, Number 6, Oct. 24, 2007, page 4. See also "Photonic gels are colorful sensors," PHYSorg.com. 10 Oct. 2012, pp. 1-3, where a clear film of polystyrene-b-poly(2-vinyl pyridine) block copolymer displayed different colors upon exposure to different anions including blue (thiocyanate), green (iodine), yellow (nitrate), orange (bromine) and red (chlorine). See further Ho Sun Lim, "Dynamic Swelling of Tunable Full-Color Block Copolymer Photonic Gels via Counterion Exchange," *ACS Nano*, 2012, 6 (10), 8933-8939 where a block copolymer comprising a hydrophobic block and a hydrophilic/polyelectrolyte block, such as polystyrene-b-poly(2-vinyl pyridine), may be employed in which the poly(2-vinyl pyridine) layers are quaternized with 1-bromoethane solution. Depending on the hydration characteristics of counteranions to which the block copolymer is exposed, the selective swelling of the block copolymer lamellar structures leads to large tunability of the photonic stop band from blue to red wavelengths.

While it is noted that the preceding block copolymer is based upon a block copolymer with a hydrophobic block (e.g., polystyrene) and a cationic hydrophilic block (e.g., poly-2-vinyl pyridine), other hydrophobic/hydrophilic block copolymers including those with a hydrophobic block and an anionic hydrophilic block and those with a hydrophobic block and a non-anionic hydrophilic block, among others, are contemplated for use in the present disclosure. Without wishing to be bound by theory, analogous to the anion exchange mechanism described above, it is believed that a block copolymer comprising a hydrophobic block and an anionic hydrophilic block may be made sensitive to cations in solution based on cation exchange.

In order to promote selective binding, binding groups that are specific to a given analyte may be included in the chemochromic material, for example, by admixing a compound having binding groups with a chemochromic material (e.g., a block copolymer) or by functionalizing a chemochromic material (e.g., a block copolymer) with binding groups. As one specific example, polystyrene-b-poly(2-vinyl pyridine) block copolymer may be chemically functionalized with 2-(bromomethyl)phenylboronic acid and cast into films that reflect a visible color when exposed to aqueous media. See O. B. Ayyub et al., *Biosensors and Bioelectronics* 28 (2011) 349-354. The 2-(bromomethyl)phenylboronic acid functionality can reversibly bind to glucose such that the polymer undergoes a shift in color when exposed to glucose.

FIG. 1A is a perspective view of a Foley catheter, according to an embodiment of the present disclosure. The catheter includes a catheter body with a proximal end 14 and a distal end (or tip) 16. The catheter also includes a catheter tube 12, balloon 18, an inflation lumen 20, and a drainage lumen 22. The balloon 18 is deflated for insertion into a patient. The balloon 18 is disposed near the distal end 16. The inflation lumen 20 extends within the catheter from the proximal end 14 to the balloon 18, and is in fluid communication with the balloon 18, for inflating and deflating the balloon 18. The distal end 16 includes an opening 26 in fluid communication with the drainage lumen 22 to facilitate drainage of urine from the bladder of a patient. The drainage lumen 22 extends within the catheter from the proximal end 14 to the opening. In the embodiment shown, a proximal portion 12c of the catheter tube is provided with chromogenic properties such that the portion 12c changes color upon exposure to an analyte of interest.

Figure 1B:
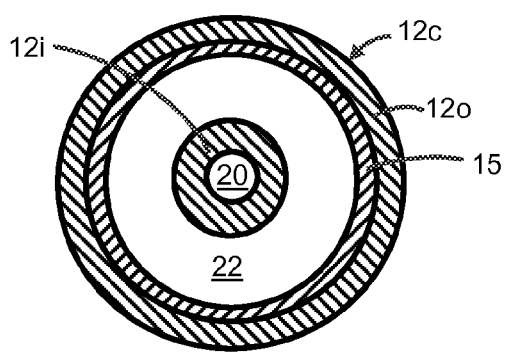
FIG. 1B is a schematic cross-sectional view taken along line B-B of FIG. 1A, in accordance with an embodiment of the present invention.

FIG. 1B is a cross-section taken along line B-B within the chromogenic portion 12c of FIG. 1A and illustrates an outer wall material 12o, an inflation lumen 20, a drainage lumen 22, an inner wall material 12i separating the inflation lumen 20 from the drainage lumen 22, and a layer of chromogenic material 15 disposed on an inner surface of the outer wall 12o. In order for a color change to be observed in the chromogenic layer 15, the outer wall 12o is preferably at least partially transparent.

Figure 2:
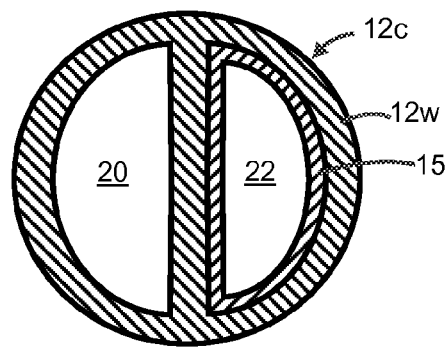
FIG. 2 is a schematic cross-sectional view taken along line B-B of FIG. 1A, in accordance with an alternative embodiment of the present invention.

Of course other cross-sectional configurations are possible. For example, FIG. 2 is an alternative cross-section taken along line B-B within the chromogenic portion 12c of FIG. 1A. FIG. 2 shows a wall material 12w, inflation lumen 20, drainage lumen 22, and a layer of chromogenic material 15 disposed on an inner surface of the wall material 12w in contact with the drainage lumen 22. As above, in order for a color change to be observed in the chromogenic layer 15, the wall material 12w is preferably at least partially transparent.

While portion 12c of the catheter tube is provided with chromogenic properties in the Figures, clearly other portions of the catheter may be rendered chromogenic. Moreover, other components not shown such as stopcocks, urine bags, etc. may be made chromogenic.

In one particular embodiment, the chromogenic portion 12c is configured to change color upon exposure to a pre-determined threshold level of cationic analyte, specifically, potassium. For this purpose, a chromogenic material 15 present on a wall of the drainage lumen 16 within portion 12c (or elsewhere) may be provided which is sensitive to potassium, for example, a block copolymer with a hydrophobic block and an anionic hydrophilic block. Potassium levels are an important indicator of kidney function and adrenal gland function. Potassium levels are also important for people being treated with medicines, such as diuretics and for people having kidney dialysis. Potassium levels are also useful in monitoring the presence of excess cell lysis (e.g., as a result of cancer treatment).

In another particular embodiment, the chromogenic portion 12c is configured to change color upon exposure to a pre-determined threshold level of glucose (e.g., in conjunction with a condition such as diabetes which is associated with high urine sugar levels). For this purpose, a chromogenic material 15 present on the wall of the drainage lumen 16 within portion 12c (or elsewhere) is preferably provided with binding groups that specifically bind to glucose such that glucose selectively is bound to the chromogenic material. As one specific example, a block copolymer comprising a hydrophobic block and a hydrophilic block, such as polystyrene-b-poly(2-vinyl pyridine) block copolymer, may be chemically functionalized with a substance that selectively binds to glucose, for example, 2-(bromomethyl)phenylboronic acid, for this purpose.

In another particular embodiment, the chromogenic portion 12c is configured to change color upon exposure to a pre-determined threshold level of an anionic analyte. For this purpose, a chromogenic material 15 present on the wall of the drainage lumen 16 within portion 12c (or elsewhere) is preferably provided which is sensitive to anion exchange. As a specific example, a block copolymer comprising a hydrophobic block and a cationic hydrophilic block, such as polystyrene-b-poly(2-vinyl pyridine) block copolymer may be employed, which is known to change to different colors with different anions.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical article configured for exposure to a bodily fluid, said medical article comprising: a chemochromic material that is present on a bodily fluid contacting surface of the medical article and exhibits a color change upon exposure to an analyte present in the bodily fluid, wherein the medical article comprises a lumen-forming component, wherein the chemochromic material is provided on an inner surface of said lumen-forming component, wherein said chemochromic material comprises a multi-layer nanostructure having first and second components of differing refractive index that are selective for binding said analyte.

2. The medical article of claim 1, wherein the first and second components of the multi-layer nanostructure comprise a block copolymer having first and second polymer blocks of differing refractive index.

3. The medical article of claim 1, wherein said first and second components of the multi-layer nanostructure comprise a block copolymer and one or more binding groups covalently attached to said block copolymer, wherein the one or more binding groups are selective for binding said analyte, and wherein said analyte is an anion, potassium or glucose.

4. The medical article of claim 1, wherein the chemochromic material is in the form of a chemochromic layer that is provided on said bodily fluid contacting surface.

5. The medical article of claim 1, wherein the lumen-forming component is transparent.

6. The medical article of claim 5, wherein the first and second components of the multi-layer nanostructure comprise a block copolymer having first and second polymer blocks of differing refractive index.

7. The medical article of claim 5, wherein the first and second components of the multi-layer nanostructure comprise a block copolymer and one or more binding groups covalently attached to said block copolymer, wherein the binding groups are selective for binding said analyte, and wherein said analyte is an anion, potassium or glucose.

8. The medical article of claim 5, wherein the medical article is a catheter, a syringe or a bodily fluid storage container.

9. The medical article of claim 5, wherein a portion of the lumen-forming surface is transparent.

10. The medical article of claim 5, wherein the analyte is potassium.

11. The medical article of claim 5, wherein the analyte is glucose.

12. The medical article of claim 1, wherein the medical article is a urine-contacting medical article or a blood-contacting medical article.

13. The medical article of claim 1, wherein the medical article is a catheter, a syringe or a bodily fluid storage container.

14. The medical article of claim 1, wherein the color change is reversible.

15. The medical article of claim 1, wherein the analyte is potassium.

16. The medical article of claim 1, wherein the analyte is glucose.

17. The medical article of claim 1, wherein the chemochromic material is a polymeric chemochromic material.

18. A method of detecting an analyte comprising: (a) contacting the medical article of claim 1 with a bodily fluid being tested for the presence of said analyte, and (b) observing a color change, if any, in the chemochromic material.

19. The method of claim 18, wherein the first and second components of the multi-layer nanostructure comprise a block copolymer having first and second polymer blocks of differing refractive index.

20. The method of claim 18, wherein the bodily fluid is urine or blood.

* * * * *